United States Patent [19]

Dybbs

[11] Patent Number: 5,308,355
[45] Date of Patent: May 3, 1994

[54] OPHTHALMIC SURGICAL INSTRUMENT AND METHOD

[76] Inventor: Alexander Dybbs, 2588 Edgerton Rd., Cleveland, Ohio 44118

[21] Appl. No.: 972,756

[22] Filed: Nov. 6, 1992

[51] Int. Cl.$^5$ ............................................. A61B 17/32
[52] U.S. Cl. ................................. 606/166; 128/661.06
[58] Field of Search ........................................ 606/4–6, 606/166, 167, 170, 172; 128/660.01, 660.06–660.08, 661.02, 661.06, 662.05, 24 AA, 745; 73/609–612, 615, 625, 628, 640, 641

[56] References Cited

U.S. PATENT DOCUMENTS

| | | | |
|---|---|---|---|
| 4,499,898 | 2/1985 | Knepshield et al. | 606/166 |
| 4,526,171 | 7/1985 | Schachar | 606/166 |
| 4,546,773 | 10/1985 | Kremer et al. | 128/660 |
| 4,637,393 | 1/1987 | Ray | 606/166 |
| 4,665,914 | 5/1987 | Tanne | 606/166 |
| 4,674,503 | 6/1987 | Peyman et al. | 606/166 |
| 4,705,037 | 11/1987 | Peyman et al. | 606/166 |
| 4,742,829 | 5/1988 | Law et al. | 128/662.05 |
| 4,817,432 | 4/1989 | Wallace et al. | 73/602 |
| 5,165,415 | 11/1992 | Wallace et al. | 128/661.06 |

OTHER PUBLICATIONS

Storz Ophthalmics Inc., "Refractive Keratoplasty" Catalogue (1992).
Chiron Ophthalmics, Brochure Entitled "Keratorefractive Surgery" (1991).
Kimi Surgical Products, Brochure Entitled "Radial and Astigmatic Keratotomy Instruments" (1992
Radial Keratotomy, LAL Publishing, Chapter 23, pp. 201–211 (1980).
Sonogage News, Sonogage, Inc.
Sonogage News, "Radial Keratotomy", Sonogage, Inc.
Information Sheet, "The Sonogage Pachometry Technique", Sonogage, Inc.
Information Sheet, "Corneo-Gage", Sonogage Corneo-Gage.

Primary Examiner—Stephen C. Pellegrino
Assistant Examiner—M. Peffley
Attorney, Agent, or Firm—Renner, Otto, Boisselle & Sklar

[57] ABSTRACT

A corneal surgical instrument comprising a surgical knife and ultrasonic probe assembly that measures the corneal thickness, monitors the positioning and perpendicularity of the knife and controls the depth of the knife blade. The ultrasonic probe assembly includes a pair of ultrasonic probes disposed on opposite sides of said cutting plane of the knife blade. Information on monitored parameters is displayed to the surgeon in the display of a surgical instrument used to perform corneal surgery.

21 Claims, 2 Drawing Sheets

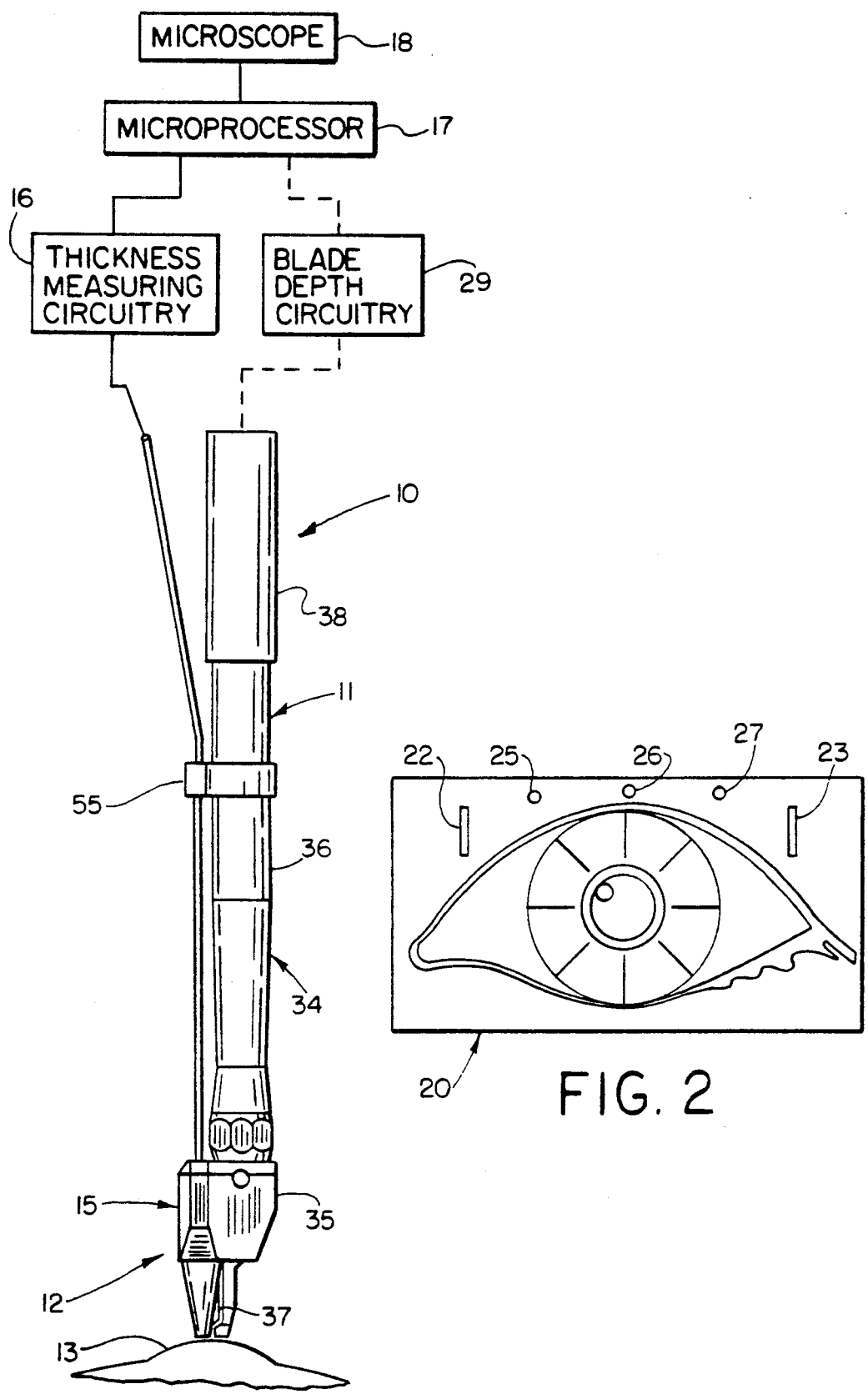

OPHTHALMIC SURGICAL INSTRUMENT AND METHOD

The invention herein described relates generally to corneal surgical procedures and instruments.

BACKGROUND

Surgical procedures to correct myopia (nearsightedness), astigmatism and hyperopia (farsightedness) have been in widespread use for at least the past 20 years. Three surgical procedures to correct these problems are radial keratotomy, astigmatic keratotomy and hexagonal keratotomy.

Radial keratotomy is used to reduce or eliminate myopia which occurs when the cornea is too steeply curved or the eyeball is too long. Blurred vision results because images focus in front of the retina. To correct for this, a series of radial incisions are made in the cornea peripherally around the central corneal zone of 3–4 mm in diameter. The incisions function to flatten the cornea and thereby move the focal point of the eye posteriorly toward the retina and ideally coincident with the retina. For optimum results, the incisions usually have to be at least 85–90% of the corneal thickness along the length thereof.

Astigmatic keratotomy corrects astigmatism caused by an irregularly shaped cornea. In an astigmatic eye, the shape of the corneal is more ovate than spherical, with the result being distorted vision. Surgical correction of the astigmatism is accomplished by placing a series of transverse incisions in opposite quadrants of the cornea. As with radial keratotomy, these incisions usually should be 85–90% of the corneal thickness.

Hexagonal keratotomy is used to correct hyperopia. Hyperopia occurs when the cornea is too flat or the eyeball is too short, whereby images focus behind the retina. To correct this problem, a "T-hexagonal" set of incisions are made in the cornea to form a six-sided geometric figure. The incisions cause the cornea inside the six-sided geometric figure to bow forward and thereby increase the curvature of the cornea and thereby move the focal point of the eye forward. This procedure has evolved since 1987 and, as currently modified by Dr. J. Charles Casebeer of Flagstaff, Ariz., has been quite successful.

At present, the above surgical procedures are for the most part done freehand by the surgeon in the following manner. The surgeon uses a pachometer, such as the Sonogage pachometer sold by Sonogage, Inc. of Cleveland, Oh., to measure the thickness of the cornea typically 1.5 mm temporal to the visual axis or several measurements are made around the periphery of the 3–4 mm central or optical zone. The lowest reading is used to set the depth of cut of a surgical knife to be used to make the incisions. The depth of cut typically is set to 85–110% of the measured minimum thickness of the cornea depending on the surgeon's previous experience.

The success of the above surgical procedures depends in part on the ability of the surgeon to guide the knife so that it is always perpendicular to the corneal surface. Cocking of the knife to either side will result in a shallower cut. Another problem is the increase in thickness of the cornea from approximately 500 microns at the optic center to approximately 580–600 microns at the periphery of the cornea. Accordingly, the percentage depth of the cut will usually decrease moving radially outwardly along the radial incision when performing radial keratotomy.

SUMMARY OF THE INVENTION

The present invention provides a corneal surgical instrument that greatly facilitates the performance of corneal surgery. The instrument comprises a cutting blade having a cutting plane and is characterized by a pair of ultrasonic probes disposed on opposite sides of said cutting plane for measuring the thickness of the cornea. This enables monitoring of the position and perpendicularity of a surgical knife including the cutting blade and to which the ultrasonic probes are mounted. Provision also is made for controlling the depth of the cutting blade and/or automatic retraction of the cutting blade if the measured thickness of the cornea is too small for the depth of cut being made.

According to a preferred embodiment of the invention, the ultrasonic probes have the axes thereof equally inclined to the cutting plane and the tips thereof positioned ahead of the cutting blade. Accordingly, the probe tips are positioned in close proximity to the cutting blade and ahead of the blade to measure the thickness of the cornea ahead of the cut. Preferably, the probe tips are laterally spaced from the cutting plane by a distance less than the lateral dimension of the probe tip and form therebetween a window through which the cutting blade can be viewed.

Further in accordance with the invention, the ultrasonic probes produce an output related to the thickness of the cornea, and provision is made for processing the outputs of the ultrasonic probes to obtain an indication of the position of the cutting blade relative to the anterior surface of the cornea. In a preferred embodiment, the surgical instrument comprises a surgical microscope having a display field, and provision is made for producing in the display field a visual indication of the position of the cutting blade relative to the anterior surface of the cornea such as its perpendicularity.

The invention also provides a holder for mounting the ultrasonic probes to a surgical knife for retrofitting existing surgical knives and/or for enabling ready removal of the ultrasonic probes. Provision also is made for processing the outputs of the ultrasonic probes to obtain a measure of the thickness of the cornea and for retracting the cutting blade as a function of the measured thickness of the cornea. Retraction of the cutting blade may be automatically effected if the measured thickness is determined to be too shallow according to a preestablished criteria.

According to another aspect of the invention, there is provided a method of performing corneal surgery, comprising the steps of continuously monitoring the perpendicularity of a surgical knife during cutting of the cornea, and producing in the display field of a surgical microscope a visual indication of when the surgical knife deviates from perpendicular by a predetermined amount. Preferably, the monitoring step includes the step of using a pair of ultrasonic probes to measure the thickness of the cornea at respective opposite sides of the cutting plane of the knife in close proximity to the cutting blade of the knife, and most preferably just ahead of the incision being made by the cutting blade.

The foregoing and other features of the invention are hereinafter fully described and particularly pointed out in the claims, the following description and the annexed drawings setting forth in detail a certain illustrative embodiment of the invention, this being indicative, however, of but one of the various ways in which the principles of the invention may be employed.

BRIEF DESCRIPTION OF THE DRAWINGS

FIG. 1 is a diagrammatic illustration of a corneal surgical instrument according to the invention.

FIG. 2 is an illustration of a display of a surgical microscope.

DETAILED DESCRIPTION

Figure 4:
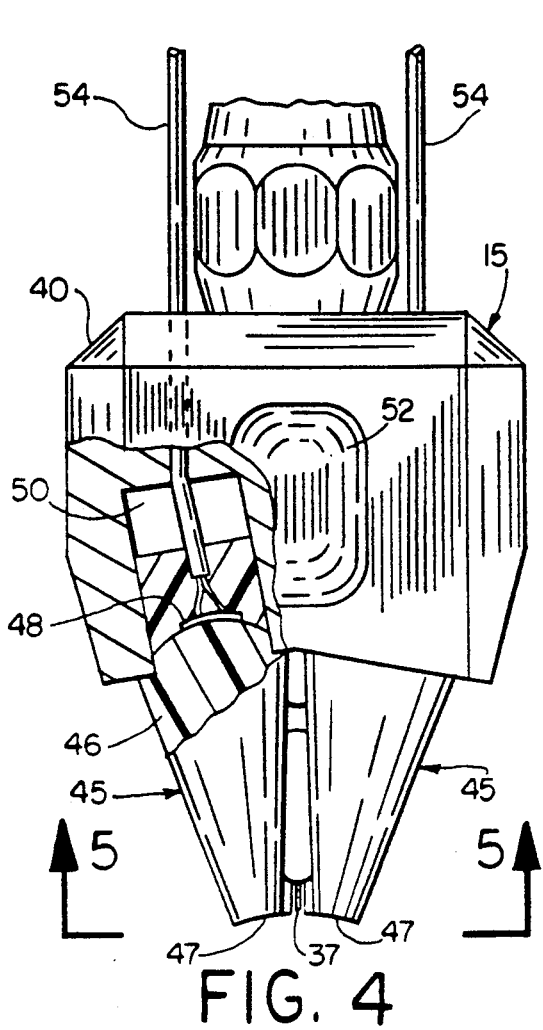
FIG. 4 is a partial top plan view, partly broken away in section, of the surgical instrument taken from the line 4—4 of FIG. 3.

Referring now in detail to the drawings and initially to FIG. 1, a surgical instrument according to the invention is indicated generally by reference numeral 10. The surgical instrument 10 generally comprises a surgical knife 11 and a thickness measuring device 12 for measuring the thickness of the cornea 13 in proximity to the cutting end of the knife. The thickness measuring device 12 comprises an ultrasonic probe assembly 15, thickness processing circuitry 16, and a microcomputer 17 that is interfaced to a surgical microscope 18.

In the manner described hereinafter in detail, the thickness measuring device 12 continuously monitors the thickness of the cornea just ahead of the incision being made by the knife 11. In addition, the thickness measuring device also indicates whether the knife is being held by the surgeon perpendicular to the surface of the cornea as is desired or is undesirably tilted to either side. This indication is provided within the eyepiece or display of the surgical microscope 18 used by the surgeon, as in the manner depicted in FIG. 2.

FIG. 2 represents a display field 20 as seen by a surgeon looking into the eyepiece or, more usually, the heads-up display of the surgical microscope 18. The positioning and perpendicularly of the knife are indicated by a pair of equal length, vertical lines 22 and 23 that are displayed at the upper left and right corners of the field 20. The equal length lines indicate that the knife 11 is being held perpendicularly to the surface of the cornea at the point that an incision is being made. If the surgeon is holding the knife tilted to either side, the lengths of the tilt indicator lines 22 and 23 may vary in relation to the angle of tilt with one line becoming shorter and the other longer to inform the surgeon that the knife blade is tilted so that appropriate corrective action may be taken. Additionally or alternatively, one of the tilt indicator lines may disappear if the degree of tilt exceeds a prescribed amount, thereby instructing the surgeon that the knife has been tilted too far to one side and that cutting should be stopped until the knife blade is righted again as indicated by the reappearance of the indicator line that had disappeared.

The thickness measuring device 12 also functions to provide in the field of view 20 of the surgical microscope an indication that the thickness of the cornea is within an acceptable range for the depth of cut being made, is too deep or is too shallow by respectively displaying a green light 25, a red light 26 or a blue light 27. Other color lights may be used, although preferably a green light is used to indicate that the procedure may proceed while a red light is used to warn that the cutting depth is too great for the measured thickness of the cornea, at which point the surgeon should cease cutting until the blade depth setting of the knife is appropriately adjusted. The lights when displayed may be steady or blinking, as desired.

The blade depth setting may be inputted into the computer 17 for comparison with the measured thickness of the cornea either manually or by use of optional blade depth circuitry 29 (FIG. 1) connected to the knife 11. As is also further discussed below, the blade depth circuitry may optionally control the cutting depth of the knife automatically in response to the measured thickness of the cornea to maintain, for example, a constant percentage thickness cut or a cut that extends to a constant distance from the posterior surface of the cornea. However, initially, the invention will be described in relation to a surgical system which employs a conventional surgical knife, as this will show how the principles of the invention may be applied to retrofit existing manually adjustable surgical knives.

In the embodiment illustrated in FIG. 1, the surgical knife 11 is a conventional knife commonly used to perform corneal surgery. In pertinent part, the knife 11 comprises a knife body 34 including a knife blade housing 35 attached to the front end of a hollow handle 36. The blade housing 35 houses a diamond cutting blade 37 which may be adjustably extended and retracted with respect to the blade housing by a micrometer adjustment knob 38 located at the rear end of the handle 36. The blade is centrally located between two guard feet 39 that are fixed to the blade housing.

Figure 3:
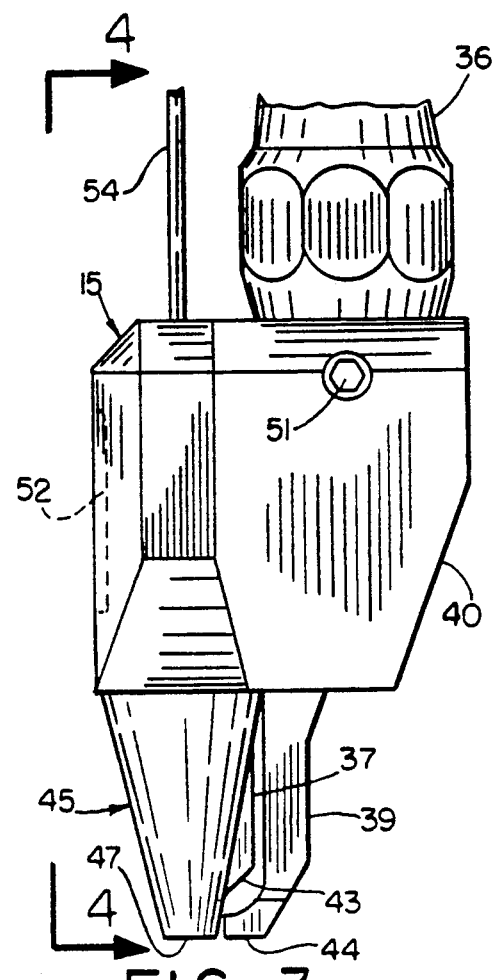
FIG. 3 is an enlarged partial side elevational view of the surgical instrument of FIG. 1 showing the cutting end of the surgical knife and ultrasonic transducer assembly thereof.

As seen in greater detail in FIG. 3, the guard feet 39 have coplanar front faces 44 intended to contact the surface of the cornea during a surgical procedure to establish a positional relationship between the knife and the cornea. Adjustment movement of the cutting blade 37 is in a direction perpendicular to the plane of the front faces 44, and the amount of extension of the cutting blade beyond the plane of the front faces 44 thereby determines the depth of penetration of the blade into the cornea. As is customary, the knife is calibrated using precision equipment so that the precise amount of extension can be selected by the surgeon by using a micrometer gauge associated with the micrometer adjustment knob 38.

The cutting end of the blade 37 has a well known configuration. The blade is a thin planar member having parallel flat sides terminating at a cutting edge 43 which is usually inclined relative to the longitudinal axis of the blade. In presently used blades, the angle formed between the cutting edge and the longitudinal axis of the blade generally is in the range of 10 to 45 degrees, although squared edge blades also are used for performing straight "T" incisions during astigmatic keratotomy.

Figure 5:
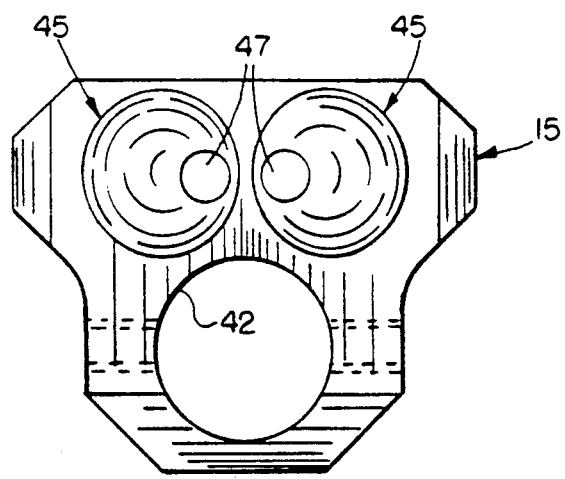
FIG. 5 is an end view of the ultrasonic transducer assembly taken from the line 5—5 of FIG. 4.

With reference FIGS. 3-5, the ultrasonic probe or transducer assembly 15 comprises a holder 40 secured to the blade housing 35 of the knife 11. In the illustrated embodiment, the holder is designed to be separable from the knife. To this end, the holder has a rearwardly opening socket 42 configured to receive with a close fit the rear barrel end of the blade housing. Since the illustrated blade housing has a cylindrical rear barrel end, the socket 42 is likewise cylindrical so that the holder may be telescopically slipped onto the blade housing. The holder is held securely, but removably, in place by a pair of diametrically opposed set screws 51 or other suitable means.

On its top surface, the holder has a shallow finger recess 52 or the equivalent as an aid in providing positive engagement with the finger of a surgeon. Many surgeons use a two-hand procedure for manipulating the knife. The handle of the knife is held by one hand while one of the fingers of the other hand, usually the index finger, is pressed against the top of the knife housing to steady and guide the cutting blade while an incision is being made. The present holder and finger recess enable a positive engagement between the surgeon's finger and the cutting end of the knife. The bottom of the finger recess may be provided with laterally extending ribs, knurling or the like.

The holder 40 functions as a mount for a pair of ultrasonic thickness measuring probes 45 that individually may be of conventional type. Accordingly, and as best seen at the left in FIG. 3, each ultrasonic probe 45 includes a conical contact head 46, also referred to as a delay line, having a circular tip 47 for contacting the surface of the cornea. At its distal end, the contact head 46 has a dome-shaped rear end surface to which an ultrasonic transducer element, i.e., a piezoelectric crystal 48, is coupled and secured in place by an epoxy backing 49. The rear end of the ultrasonic probe 45 is fixed in a cylindrical socket 50 in the holder.

The piezoelectric crystal 48 of each ultrasonic probe 45 is operatively connected to the wire leads of an electrical cable 54 which extends out through the back end of the holder for connection to the thickness measuring circuitry 16 (FIG. 1). Preferably, the cable 54 is run along the length of the knife body and held in place by one or more retention bands 55.

As is well known, the circuitry 16 may be operated to pulse the piezoelectric crystal in order to generate a 20 MHz beam. The beam is directed along the axis of the contact head which focusses the beam at a point located forwardly of the probe tip 47 so that the focal point will lie interiorly of the cornea when the probe tip contacts the outer surface of the cornea. The 20 MHz pulse that is generated will result in a first echo corresponding to the anterior corneal surface and a second echo corresponding to the posterior corneal surface. The difference in time of these two echoes received back at the transducer 48 is a measure of the corneal thickness, as the time between the reflected echoes can be converted in known manner to a distance which will be the thickness of the cornea along the probe axis at the point the probe contacts the cornea. By repeatedly pulsing the transducer and detecting the echoes, the thickness of the cornea may be continuously monitored and reported by the depth measuring circuitry to the computer 18, respectively. Individually, the ultrasonic probes and associated ultrasonic depth measuring circuitry have been used in prior art devices including, in particular, Sonogage pachometers sold by Sonogage, Inc. of Cleveland, Oh.

Although the ultrasonic probes 45 individually fall within the prior art as just indicated, two such probes are uniquely combined and related to a surgical knife in a manner that overcomes problems associated with prior art corneal surgical equipment and procedures. As seen in FIGS. 3-5, the two probes 45 are located at respective opposite sides of the cutting plane of the cutting blade with the axes thereof preferably residing in a common plane that is parallel to the longitudinal axis of the cutting blade and perpendicular to the cutting plane of the cutting blade or, more generally, perpendicular to the cutting direction of the cutting blade.

In general, the cutting plane of the cutting blade is the plane defined by the longitudinal axis of the cutting blade and the direction in which the blade is intended to cut (the cutting direction in FIG. 3 is right to left). In the case of a flat planar cutting blade as shown, the cutting plane of the cutting blade coincides with the major planar extent of the cutting blade. What is desired is that the ultrasonic probes and, more particularly, the tips thereof are disposed on opposite sides of the movement path of the blade and equally laterally spaced from such movement path.

In addition, the probes preferably are oriented to bring the tips thereof into close proximity to the movement path of the cutting blade. To this end, the probes are inclined in the common plane thereof such that their axes are inclined to the cutting plane of the cutting blade at the same included angle. In the illustrated embodiment, the axis of each probe forms with the cutting plane of the cutting blade an angle of about 10 degrees. Moreover, the axes of the two probes preferably intersect at a point located about 7.50 mm in front of their probe tips, such dimension being about the average radius of curvature of the cornea. Accordingly, the probe axes will extend perpendicularly to the anterior surface of the cornea when the longitudinal axis of the knife is perpendicular to such surface. The longitudinal axis of the knife bisects the angle formed between the axes of the probes.

In addition, the tips of the probes are located ahead of the feet 39 and more particularly the cutting blade. As a result, the probes will operate to measure the thickness of the cornea ahead of the cutting blade rather than coincidentally with the cut. This affords better protection in those situations where the thickness of the cornea varies rapidly and unexpectedly as the cut is being made. In an alternative embodiment, the probes may function as the feet whereby the feet may be eliminated. In this alternative arrangement, the probe tips preferably are substantially disposed in the same plane as the cutting blade rather than spaced ahead of the cutting blade.

In the illustrated embodiment, the tips of the probes are spaced ahead of the cutting edge of the cutting blade by about 2 mm. Each probe tip has a diameter of about 1.5 mm and the tips are laterally spaced apart to provide a window having a width of about 0.7 mm through which the cutting blade can be viewed by the surgeon when making an incision. Of course, such window will appear relatively large when viewed on the heads-up display of the surgical microscope. If desired, the width of the window may be increased by more sharply tapering the adjacent inner sides of the conical contact heads.

As seen in FIGS. 3 and 4, the tips of the probes are tangential to an arc common with the front faces 44 of the feet 39. That is, the probe tips will contact the cornea when the feet are brought into contact with the cornea, provided the knife is oriented perpendicularly to the anterior surface of the cornea. If the knife is tilted to either side, this will be detected in the below described manner. If the knife is tilted in a direction opposite the cut direction, this will lift the probes out of contact with the cornea and this will be indicated by the spurious readings received by the computer. Regarding tilting of the knife in the direction of cutting movement, this normally will occur infrequently and the only consequence is a shallow cut. Also, such tilting will give a false reading that the thickness is greater than it actually is until the probes are sufficiently tilted that they will provide spurious measurements to the computer.

In use, the two probes 45 are used to make corneal thickness measurements. The measurements may be based on an averaging of multiple, such as 500, sets of echoes that are sampled from each transducer. The microprocessor takes the thickness measurements made by the two transducers at the same or substantially the same time and compares them. If the difference between the two thickness measurements is greater than a prescribed amount, such as 5 microns, then a signal is sent to the display 20 to indicate an unacceptable degree of knife tilt, such as by blanking out the vertical lines 22 and 23, causing the tilt indicator lines to blink, or other indicating scheme that may be desired. If the difference is less than the prescribed amount, the tilt indicator lines may remain uniform. Accordingly, the difference between the thickness measurements made by the transducers is used to detect an unacceptable degree of knife tilt in a direction perpendicular to the direction of cutting movement of the knife, i.e., a measure of the perpendicularity of the cutting plane of the blade relative to the anterior surface of the cornea.

The two thickness measurements also are averaged and compared to the blade setting that has been inputted into the computer or automatically sensed by the blade depth circuitry 29 (FIG. 1). If the average measurement is within a prescribed amount, for example 5 microns, of the blade setting value, the green light on the display 20 is turned on to inform the surgeon that the cornea thickness is within an acceptable range, such as plus or minus 5 microns of the set amount. If the blade setting exceeds the average measured thickness by more than the prescribed amount, the red light is blinked to warn of too deep of cut. If the average measured thickness exceeds the blade setting by more than the prescribed amount, the blue light is blinked to warn that the cut is too shallow.

Preferably the foregoing measurement and comparison operations are repeated continuously at a suitable frequency of say 10 times a second.

As above indicated, the blade depth circuitry 29 (FIG. 1) may have provision for automatically controlling the cutting depth of the knife in response to the measured thickness of the cornea to maintain, for example, a constant percentage thickness cut or a cut that extends to a constant distance from the interior surface of the cornea. In this modified arrangement, the adjustment knob 38 (FIG. 1) may be replaced by a suitable blade drive mechanism including, for example, a stepping motor and appropriate circuitry for operating the stepping motor and providing positive feedback of the cutting depth of the blade. Then, the position of the blade may be controlled by the computer in programmed response to cornea thickness measurements made by the ultrasonic probes. If the measured thickness is less than the blade depth setting by a prescribed amount, the computer not only can provide the above described visual warning to the surgeon but it can also automatically retract the cutting blade. In a more automated system, the microprocessor may be programmed to automatically vary the cutting depth of the cutting blade in response to the measured thickness of the cornea to maintain, for example, a constant percentage thickness cut or a cut that extends to a constant distance from the posterior surface of the cornea.

As above described and shown in FIGS. 3–5, the probe assembly is a separate structure that can be assembled onto and removed from the knife. As above indicated, this lends itself to retrofitting existing surgical knives. Additionally, the probe assembly may be removed for sterilization apart from the knife or for disposal and replacement with another probe assembly. Notwithstanding these advantages, the invention also contemplates an integrated knife and probe assembly wherein the probes are integrally assembled into the knife body independently of any removable holder. This will provide for a more compact structure and will allow the probe wiring to be run through the knife body.

Another advantage afforded by the invention is a self-checking feature that arises from the use of two probes for measuring the thickness of the cornea. If one probe goes bad and starts giving incorrect thickness readings, this will become immediately evident by comparison with the readings provided by the still properly functioning probe. By virtue of the foregoing logic, the surgeon will be informed that he has lost perpendicularity. Upon realizing that in fact he has not lost perpendicularity, the surgeon will know that there is a malfunction in the system.

Although the invention has been shown and described with respect to certain preferred embodiments, equivalent alterations and modifications will no doubt occur to others skilled in the art upon the reading and understanding of this specification. The present invention includes all such equivalent alterations and modifications, and is limited only by the scope of the following claims.

What is claimed is:

1. A surgical instrument for making incisions in the cornea of an eye comprising a knife body and a cutting blade connected to the knife body, the cutting blade having a cutting plane, and the surgical instrument being characterized by a pair of ultrasonic probes connected to the knife body and disposed on opposite sides of the cutting plane for measuring the thickness of the cornea, the ultrasonic probes each having a probe tip for contacting the cornea, and each said probe tip being laterally spaced apart from the other to form therebetween a window through which the cutting blade can be viewed.

2. A surgical instrument as set forth in claim 1, wherein the ultrasonic probes each has an axis inclined to the cutting plane.

3. A surgical instrument as set forth in claim 2, wherein the ultrasonic probes are disposed ahead of the cutting blade in relation to a cutting direction of the cutting blade.

4. A surgical instrument as set forth in claim 3, wherein the ultrasonic probes have the axes thereof disposed in a plane extending perpendicular to the cutting plane.

5. A surgical instrument as set forth in claim 1, wherein the ultrasonic probes are disposed ahead of the cutting blade in relation to a cutting direction of the cutting blade.

6. A surgical instrument as set forth in claim 1, wherein each said probe tip has a lateral dimension and each said probe tip is laterally spaced from the cutting plane by a distance less than the lateral dimension of the probe tip.

7. A surgical instrument as set forth in claim 1, wherein the ultrasonic probes produce an output related to the thickness of the cornea, and further comprising means for processing the outputs of the ultrasonic probes to obtain an indication of the position of the cutting blade relative to the anterior surface of the cornea.

8. A surgical instrument as set forth in claim 7, comprising a surgical microscope having a display field, and means connected to the processing means for producing in the display field a visual indication of the position of the cutting blade relative to the anterior surface of the cornea.

9. A surgical instrument as set forth in claim 7, wherein the processing means includes means for comparing the outputs of the probes to provide a measure of the perpendicularity of the cutting plane of the blade relative to the anterior surface of the cornea.

10. A surgical instrument as set forth in claim 1, comprising a surgical knife including the cutting blade, the knife body, and means for mounting the cutting blade to the knife body for extension and retraction relative to the knife body, and means for mounting the ultrasonic probes to the knife body.

11. A surgical instrument as set forth in claim 10, wherein the means for mounting includes a holder for the ultrasonic probes, and the holder includes means enabling its ready removal from the knife body.

12. A surgical instrument as set forth in claim 11, wherein said holder has a top surface including a finger depression.

13. A surgical instrument as set forth in claim 10, wherein the ultrasonic probes produce an output related to the thickness of the cornea, and further comprising means for processing the outputs of the ultrasonic probes to obtain a measure of the thickness of the cornea, and means for retracting the cutting blade as a function of the measured thickness of the cornea.

14. A surgical instrument as set forth in claim 13, wherein the function effects retraction of the cutting blade if the measured thickness is determined to be too shallow according to a preestablished criteria.

15. A surgical instrument as set forth in claim 10, wherein the ultrasonic probes produce an output related to the thickness of the cornea, and further comprising means for processing the outputs of the ultrasonic probes to obtain a measure of the thickness of the cornea, a surgical microscope having a display field, and means connected to the processing means for producing in the display field a visual warning if the measured thickness is determined to be too shallow according to a preestablished criteria.

16. A surgical instrument as set forth in claim 15, wherein the processing means includes means for comparing the outputs of the probes to provide a measure of the perpendicularity of the cutting plane of the blade relative to the anterior surface of the cornea.

17. A surgical instrument as set forth in claim 1, comprising a pair of guard feet on the knife body and disposed on opposite sides of the cutting plane laterally adjacent the cutting blade, and wherein the ultrasonic probes are disposed ahead of the guard feet in relation to a cutting direction of the cutting blade.

18. An ultrasonic probe assembly for mounting to a body of a surgical knife having a cutting blade defining a cutting plane, said assembly comprising a holder adapted to be mounted to the knife body, and a pair of ultrasonic probes supported in said holder such that the ultrasonic probes will be disposed on opposite sides of the cutting plane for measuring the thickness of the cornea, the ultrasonic probes each having a probe tip for contacting the cornea, and each said probe tip being laterally spaced apart from the other to form therebetween a window through which the cutting blade can be viewed when the holder is mounted to the knife body.

19. A surgical instrument as set forth in claim 18, wherein the ultrasonic probes produce an output related to the thickness of the cornea, and further comprising means for processing the outputs of the ultrasonic probes to obtain a measure of the thickness of the cornea.

20. A surgical instrument as set forth in claim 19, wherein said processing means includes means for comparing the outputs of the probes to provide a measure of the perpendicularity of the cutting plane of the blade relative to the anterior surface of the cornea.

21. A surgical instrument as set forth in claim 18, wherein the ultrasonic probes produce an output related to the thickness of the cornea, and further comprising means for processing the outputs of the ultrasonic probes to obtain a measure of the thickness of the cornea, a surgical microscope having a display field, and means connected to the processing means for producing in the display field a visual warning if the measured thickness is determined to be too shallow according to a preestablished criteria.

* * * * *